United States Patent [19]

Zukowski

[11] 4,390,018
[45] Jun. 28, 1983

[54] METHOD FOR PREVENTING LOSS OF SPINAL FLUID AFTER SPINAL TAP

[76] Inventor: Henry J. Zukowski, 72 N. Deeplands Rd., Grosse Pointe Shores, Mich. 48236

[21] Appl. No.: 379,109

[22] Filed: May 17, 1982

Related U.S. Application Data

[62] Division of Ser. No. 187,354, Sep. 15, 1980, abandoned.

[51] Int. Cl.³ .............................................. A61B 17/00
[52] U.S. Cl. ................................ 128/303 R; 128/325; 128/763
[58] Field of Search ................................ 128/763–766, 128/748, 325, 303 R, 303 B, 127, 341, 1 R; 604/374, 358, 385, 362, 11

[56] References Cited

U.S. PATENT DOCUMENTS

| | | | |
|---|---|---|---|
| 2,396,351 | 3/1946 | Thompson | 128/748 |
| 3,858,571 | 1/1975 | Rudolph | 128/341 X |
| 3,941,127 | 3/1976 | Froning | 128/303 B X |
| 4,030,504 | 6/1977 | Doyle | 128/325 |
| 4,230,117 | 10/1980 | Anichkov | 128/303 B |

FOREIGN PATENT DOCUMENTS 737405  6/1980  U.S.S.R. ............................. 128/325

*Primary Examiner*—Michael H. Thaler
*Attorney, Agent, or Firm*—Barnes, Kisselle, Raisch, Choate, Whittemore & Hulbert; Barnes, Kisselle, Raisch, Choate, Whittemore & Hulbert

[57] ABSTRACT

A method and apparatus for sealing a hole in the spinal canal of a patient made by a needle used to make a spinal tap. An elongated hemostatic thread is inserted into the lumen of the needle before the needle is removed from the patient after making a spinal tap and while the tip of the needle remains disposed in the hole in the spinal canal formed during penetration thereof by the needle. A wire inserted in the lumen of the needle is employed to advance the hemostatic member to the tip of the needle and to prevent withdrawal of the hemostatic member with the needle when the latter is subsequently withdrawn so that the hemostatic member will remain in situ in the hole as a plug to seal the same.

7 Claims, 4 Drawing Figures

U.S. Patent  Jun. 28, 1983  4,390,018
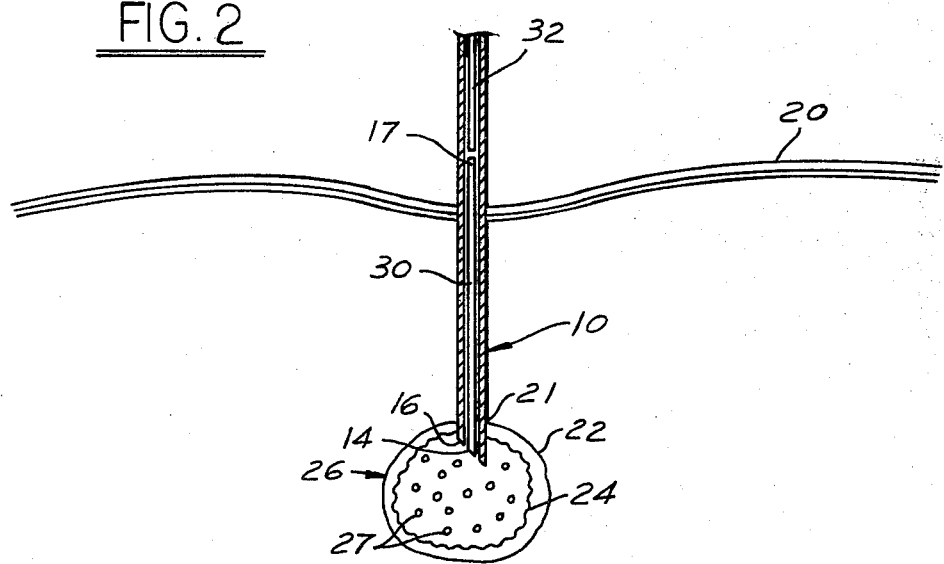
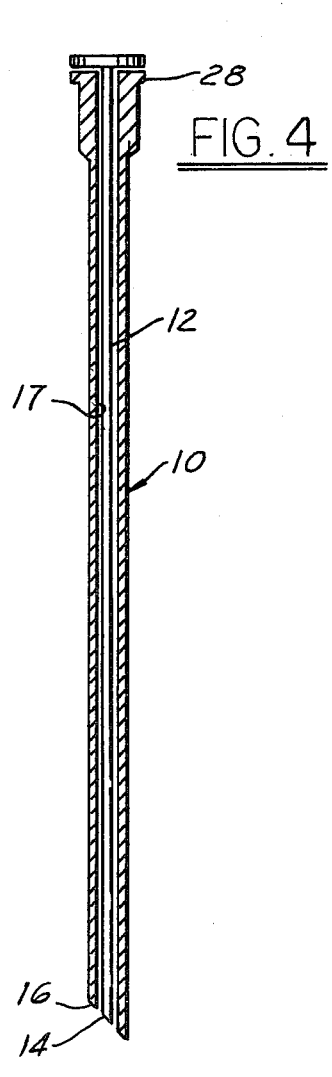
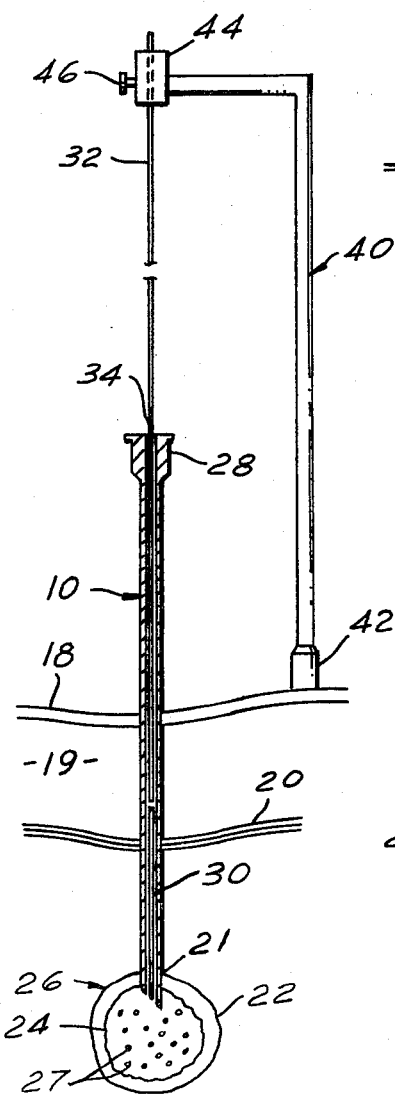
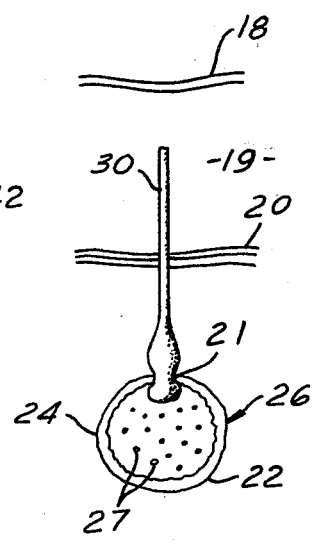

METHOD FOR PREVENTING LOSS OF SPINAL FLUID AFTER SPINAL TAP

This is a division of application Ser. No. 187,354, filed Sept. 15, 1980, now abandoned.

This invention relates generally to a method of and apparatus for sealing a hole in the spinal canal of a patient made by a needle used to make a spinal tap.

BACKGROUND AND SUMMARY OF THE INVENTION

Insertion of a needle into the spinal canal through the midline of the back is an established medical procedure. The purpose of such a needle insertion is (1) to obtain a sample of spinal fluid for analysis, (2) to inject medications or contrast media as in x-ray examinations, or (3) to inject local anesthetic solutions for surgical anesthesia, pain control or diagnostic procedures.

A complication of this procedure is the so-called post spinal tap headache. The purpose of this invention is the prevention of this complication.

The spinal canal begins at the base of the skull and extends downward, encased in the vertebral column, to the sacrum. It contains the spinal cord which is an extension of the brain stem. It terminates at approximately the 1st lumbar vertebra. It also contains the spinal nerves which extend from the cord to points of exit from the canal. The spinal canal is filled with a fluid which at its upper limit is continuous with a similar system that encases the brain, the fluid systems being the same and serving the same purpose: cushioning the nerve tissues they contain.

To enter the spinal canal, needle insertion is usually below the level of the 1st lumbar vertebra so as not to strike the spinal cord. Traversing the skin, subcutaneous tissues and fascial planes produces no lasting untoward effect. However, when the needle enters the dura and pia mater a hole is produced which, because of the fibrous nature of the dura, tends to remain open after the needle is withdrawn. Spinal fluid leaks out of this hole into the surrounding tissues and is absorbed. As spinal fluid is lost, the cushioning effect on the nerve tissues of the system also is lost. The resulting hypovolemia of spinal fluid makes itself apparent when the subject of the spinal tap goes from the supine to erect position. All the tissues of the canal system including the brain gravitate downward due to the lack of spinal fluid cushion. As the brain gravitates down, pull on structures attached to the brain and skull produce pain which is interpreted by the subject as headache, usually severe and incapacitating.

The cause of the headache following spinal tap is the hole produced in the dura mater at the time of needle insertion. This invention seeks to seal the hole on needle withdrawal so that loss of spinal fluid is prevented.

BRIEF DESCRIPTION OF THE DRAWINGS

FIG. 1 is a side elevational view with parts in section of apparatus employed in the practice of my invention.

FIG. 2 is an enlarged sectional view showing a portion of FIG. 1.

FIG. 3 illustrates a hemostatic member in situ in the hole in the spinal canal of a patient made by the needle used to make a spinal tap, after the needle has been withdrawn.

FIG. 4 is an enlarged sectional view of a typical needle and stylet used for a spinal tap, the needle without the stylet being shown as part of the apparatus in FIGS. 1 and 2.

DETAILED DESCRIPTION

The needle used for a spinal tap is a familiar medical instrument and is indicated at 10 in FIG. 4. The needle 10 is standardized as to length and diameter and varies from other needles in that it contains a stylet 12 whose tip 14 is ground down flush with the cutting tip 16 of the needle. The stylet is an elongated rod-like member which extends lengthwise within the bore or lumen 17 of the needle to prevent clogging as the needle advances through tissues. During the advance of the needle, it traverses the skin 18, subcutaneous tissues 19 and fascial planes 20 to a position of final placement in which its tip 16 forms a hole 21 in the dura 22 and pia mater 24 in the spinal canal 26. The numeral 27 designates spinal nerves in the canal. After final placement, the stylet is removed and spinal fluid is withdrawn from the spinal canal through the needle in a well-known manner. A drip of spinal fluid from the hub 28 of the needle signals a successful tap.

FIGS. 1 and 2 show the needle in the final placement position it occupies during and after the spinal tap in which its tip remains disposed in the hole 21 in the spinal canal. The stylet, of course, has been removed at this point in the procedure since the spinal tap has already been completed.

In order to seal the hole 21 in the spinal canal formed by the needle, a hemostatic member 30 in the form of an elongated element of approximately the same diameter as the stylet is inserted into the lumen of the needle through the hub end. This hemostatic element is preferably in the form of a thread of oxidized regenerated cellulose. A relatively rigid, elongated member or wire 32, also of approximately the same diameter as the stylet, is then inserted in the hub end of the needle behind the hemostatic member and is advanced into the needle to push the hemostatic member ahead of it down to the tip of the needle. A mark 34 may be provided on the wire so that advancing the wire into the lumen up to the mark at the hub will force the hemostatic member 30 to the tip of the needle but no further. It will be understood that all of the foregoing steps to seal the hole are carried out before the needle is removed from the patient and while the tip of the needle remains disposed in the hole in the spinal canal in the position it occupied during the spinal tap.

The wire 32 is then held in the position shown in FIG. 1 and the needle 10 is withdrawn over the wire, leaving the hemostatic member 30 in situ in the hole as a plug to seal the same. In this position, the hemostatic member is preferably just a few millimeters inside the spinal canal, the remaining portions of the hemostatic member resting in the tissues overlying the dura.

Oxidized regenerated cellulose is preferred as a material for the hemostatic member 30. This material is manufactured in woven sheet form by Johnson & Johnson Company under the trademark SURGICEL for use in surgery to aid in hemostasis. Application of this material to an oozing surface is effective in stopping bleeding. Although the mechanism for doing so is not well understood, it has been proven effective and is widely used. One of its characteristics is that it swells as it absorbs blood or any other fluid. This characteristic is important in its application to the present invention.

Woven threads of the oxidized regenerated cellulose material referred to above are also available. As stated above, the hemostatic member 30 is preferably formed of a woven thread of such oxidized regenerated cellulose material. After the needle 10 is withdrawn, leaving the thread 30 in situ in the hole as a sealing plug, the cellulose material of the hemostatic member begins to swell to produce a dumbbell-shaped occlusion of the hole in the dura, effectively stopping spinal fluid. See FIG. 3. Healing of the dural hole is effected by dural proliferation through the cellulose plug which is absorbed over a period of time.

Removal of the needle over the wire is a critical maneuver. Displacement of the wire too deeply or not deeply enough would prevent the correct placement of the cellulose thread. Therefore, a stabilizing stand or arm 40, such as the one in FIG. 1, is recommended to hold the wire in fixed position as the needle is removed. The stand has a base 42 at one end to be supported and rest upon the body of the patient. The other end of the stand has a head 44 provided with a through passage in which the wire is longitudinally adjustably received. A set screw 46 threaded into the head is provided to secure the wire in the passage in longitudinally adjusted position.

The thread of oxidized regenerated cellulose is preferably treated to slightly delay expansion when it contacts spinal fluid in the needle before the needle is withdrawn. The thread may, for example, be treated with starch to delay expansion. Oxidized regenerated cellulose is not the only material which may be used as the material of the hemostatic member. Catgut or cotton might also be used. All of these materials are biocompatible.

I claim:

1. A method of sealing a hole in the spinal canal of a patient made by a needle used to make a spinal tap, comprising inserting a member, capable of swelling on contact with body fluid, into the lumen of the needle before removing the needle from the patient after making a spinal tap and while the tip of the needle remains disposed in the hole in the spinal canal formed during penetration thereof by the needle, advancing said member to the tip of the needle, and thereafter withdrawing the tip of the needle without withdrawing said member so that said member will remain in situ in the hole as a plug and will swell by reason of contact with body fluid to effectively seal the hole.

2. A method as defined in claim 1, wherein said member is made of material selected from the group consisting of oxidized regenerated cellulose, catgut, and cotton.

3. A method as defined in claim 1, wherein said member is oxidized regenerated cellulose.

4. A method as defined in claim 1, wherein said member is made of a biocompatible material.

5. A method as defined in claim 1, wherein a wire is inserted into the needle to advance said member as aforesaid which wire is held stationary during withdrawal of the needle to prevent said member from being withdrawn with the needle.

6. A method as defined in claim 5, wherein said wire bears a mark to facilitate insertion thereof with precision.

7. A method as defined in claim 1 or 6, wherein said member is an elongated thread made of oxidized regenerated cellulose.

* * * * *